(12) United States Patent
Stanley et al.

(10) Patent No.: US 10,172,683 B2
(45) Date of Patent: Jan. 8, 2019

(54) MEASURING DEVICES FOR MEDICAL TOOLS

(71) Applicants: Anthony G. Stanley, North Bay Village, FL (US); Donald L. Huzzie, Sr., Miami Gardens, FL (US)

(72) Inventors: Anthony G. Stanley, North Bay Village, FL (US); Donald L. Huzzie, Sr., Miami Gardens, FL (US)

( * ) Notice: Subject to any disclaimer, the term of this patent is extended or adjusted under 35 U.S.C. 154(b) by 218 days.

(21) Appl. No.: 15/045,612

(22) Filed: Feb. 17, 2016

(65) Prior Publication Data

US 2016/0235498 A1 Aug. 18, 2016

Related U.S. Application Data

(60) Provisional application No. 62/117,731, filed on Feb. 18, 2015.

(51) Int. Cl.
*A61B 17/04* (2006.01)
*A61B 90/00* (2016.01)
(Continued)

(52) U.S. Cl.
CPC .......... *A61B 90/06* (2016.02); *A61B 17/0483* (2013.01); *A61B 17/282* (2013.01); *A61B 17/285* (2013.01); *A61B 17/2812* (2013.01); *A61B 2017/3405* (2013.01); *A61B 2090/061* (2016.02); *A61B 2090/067* (2016.02)

(58) Field of Classification Search
CPC . A61B 90/06; A61B 17/0483; A61B 17/2812; A61B 17/29; A61B 2017/3405; A61B 17/285; A61B 17/28; A61B 2090/067; A61B 2090/061; A61B 17/282; A61B 17/295; A61B 2017/2901; A61B 2017/2926; A61B 17/2804; A61B 2017/2808; A61B 17/3201; A61B 17/08; A61B 2017/081; B25B 7/22; B25B 7/02; B25B 5/04; B25B 5/16; B25B 5/163; B25B 5/166

See application file for complete search history.

(56) References Cited

U.S. PATENT DOCUMENTS 3,808,915 A * 5/1974 Bonnel, Sr. ............ A01K 97/18
7/106
5,033,195 A 7/1991 Appelkvist et al.
(Continued)

OTHER PUBLICATIONS

Aspen Medical Europe Ltd., "Bard-Parker® Protected Disposable Scalpels" product information sheets; printed Mar. 9, 2016; 2 pages; (downloadable .pdf—see http://www.aspenmedicaleurope.com/surgical_products/bard-parker-protected-disposable-scalpels/).

(Continued)

*Primary Examiner* — Katrina Stransky
(74) *Attorney, Agent, or Firm* — Dority & Manning, P.A.

(57) ABSTRACT

Measuring devices that can be incorporated with gripping tools are described. The measuring devices can be integral to a gripping tool or can be removably attachable to a gripping tool. The measuring devices can be incorporated in conjunction with a gripping tool for use in a medical application such as a clamp, a hemostat, a forceps, or the like. Devices can be utilized to determine a straight length and/or to determine the spread of the jaws a gripping tool associated with the device.

16 Claims, 10 Drawing Sheets

(51) Int. Cl.
   *A61B 17/28* (2006.01)
   *A61B 17/285* (2006.01)
   *A61B 17/34* (2006.01)

(56) References Cited

U.S. PATENT DOCUMENTS

| | | | |
|---|---|---|---|
| 5,365,625 | A | 11/1994 | Han |
| 5,383,274 | A | 1/1995 | Miller |
| 5,484,447 | A * | 1/1996 | Waldock ............ A61B 17/0231 33/511 |
| 6,324,712 | B1 | 12/2001 | Elsener, Sr. |
| 7,021,177 | B2 | 4/2006 | Lovemark et al. |
| 7,111,376 | B2 | 9/2006 | Lombardi et al. |
| 8,522,443 | B2 | 9/2013 | Latronico et al. |
| 2006/0236548 | A1 | 10/2006 | Namvar |
| 2007/0156162 | A1 * | 7/2007 | Kammerer ......... A61B 17/2812 606/174 |
| 2009/0078278 | A1 | 3/2009 | Tran |
| 2009/0149868 | A1 | 6/2009 | Shelton et al. |
| 2009/0241342 | A1 | 10/2009 | Habib |
| 2009/0293686 | A1 | 12/2009 | Pfab |
| 2012/0136364 | A1 * | 5/2012 | Teramoto ............... A61C 1/084 606/102 |
| 2013/0197516 | A1 * | 8/2013 | Kappel ................. A61B 17/29 606/46 |
| 2014/0343561 | A1 * | 11/2014 | Penzimer ........... A61B 17/7074 606/102 |
| 2015/0375385 | A1 * | 12/2015 | Nix ........................ B25F 1/003 362/119 |

OTHER PUBLICATIONS

AVEN website; http://www.aveninc.com/avens-complete-product-line/tools/pliers-and-cutters/accu-cut-premium-pliers-and-cutters/accu-cut-xl-oval-head-cutter-2#,U-IOImd3uM8; webpage printed Sep. 25, 2015; (4 pages).

Ted Pella, Inc website; http://www.tedpella.com/tools_html/cutters.htm#_oval ; webpage printed Sep. 25, 2015; (8 pages).

Stantley pliers #89-858 Fat Max—3 Photos. Printed Sep. 25, 2015; (3 pages).

Knipex diagonal cutters; http://www.zoro.com/knipex-diagonal-cutters-7-14-in-74-12-160/1/G6419585/; webpage printed Sep. 25, 2015; (2 pages).

Lindstrom; PDF catalogue; p. 31; printed Sep. 28, 2015; http://www.google.com/url?sa=t&rct=j&q=&esrc=s&source=web&cd=8&vcd=0CFAQFjAHahUKEwjmu7zAk5bHAhXEbD4KHSIOB4c&url=http%3A%2F%2Fwww.lindstromtools.com%2Fpdf_down.php&ei=djbEVeaoNMTZ-OGinJy4CA&usg=AFQiCNEngyRCOyyTghhtlGbVWqEtR5BsGw&bym=bv.99804247.d.cWw.

Swanstrom Tools USA; http://www.swanstromtools.com/choose.htm ; printed Sep. 14, 2015; (4 pages).

Stanley, Dr. Anthony G.; International Patent Application No. PCT/US15/44976; International Search Report; dated Nov. 23, 2015; 2 pages.

Stanley, Dr. Anthony G.; Related Application—U.S. Appl. No. 14/825,306, filed Aug. 13, 2015.

* cited by examiner

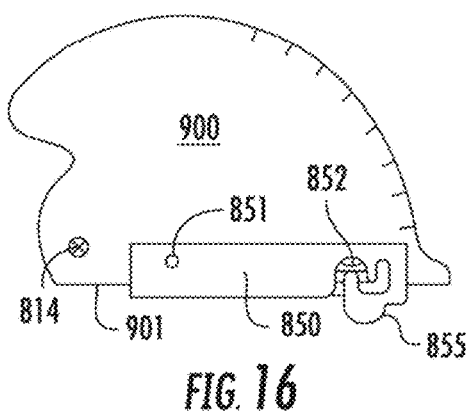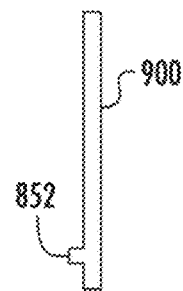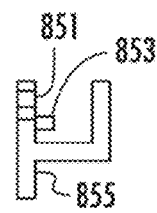
FIG. 16    FIG. 17    FIG. 18
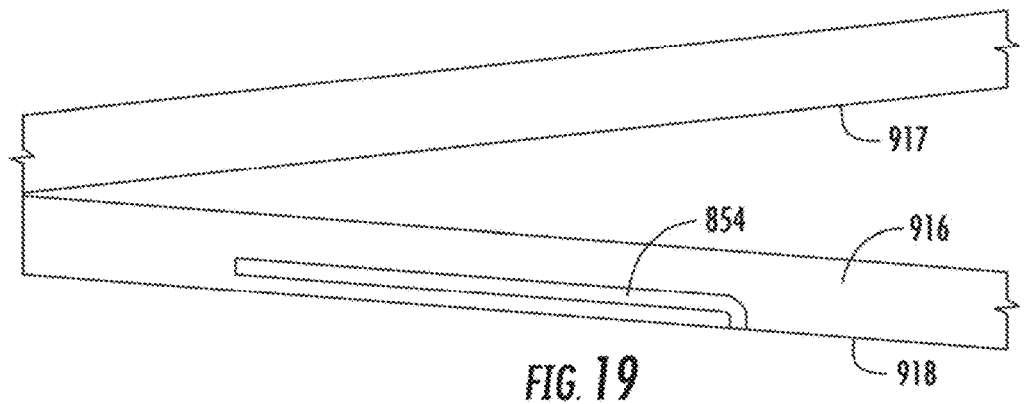
FIG. 19
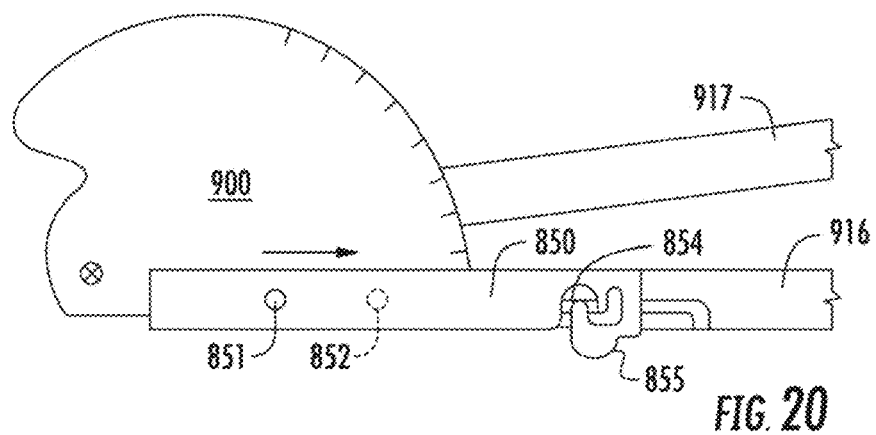
FIG. 20

MEASURING DEVICES FOR MEDICAL TOOLS

CROSS REFERENCE TO RELATED APPLICATION

This application claims filing benefit of U.S. Provisional Patent Application Ser. No. 62/117,731, having a filing date of Feb. 18, 2015, which is incorporated herein by reference in its entirety.

BACKGROUND

During medical procedures, the need often arises to measure distances of a relatively small size such as puncture depths, foreign object sizes, wound sizes, abscess sizes, and the like. Such dimensions are often necessary to gauge the level and type of care required for a patient. Moreover, this need is also becoming necessary for administrative purposes. For instance, proper and timely insurance remuneration can depend upon the accurate reporting of the details of a medical procedure including the dimensions of embedded objects, wounds, etc. Three typical such situations are illustrated in FIG. 1, FIG. 2, and FIG. 3. FIG. 1 illustrates a foreign object 10 in a patient's foot and FIG. 2 illustrates a foreign object 12 in a patient's nose, such foreign objects must be described in required written reports according to size, location, etc. and can require different treatment options depending on their size, depth, etc. FIG. 3A illustrates a facial laceration 3 and FIG. 3B illustrates the laceration following suturing. Both the overall wound size and the laceration description must include dimensional information for both medical and administrative purposes.

FIG. 4 illustrates a common damping tool (a hemostat) that is used in medical procedures to clamp and manipulate physiological structures as well as to grip, stabilize, and remove foreign objects embedded in a body. Unfortunately, a separate instrument is presently required to provide information with regard to distances such as in situ depth and/or size of an embedded foreign object, size of a wound, etc. While foreign objects can be measured following removal, in situ measurement is desirable to properly obtain not only the subdermal depth of the object but also to be sure that the entire object is removed via post-removal measurement confirmation.

In response to such medical needs and administrative requirements, suggestions have been put forth to include measuring devices in sterile procedure trays. While this would be of benefit, it would also increase the size and cost of sterile trays as well as the amount of waste associated with a procedure.

What are needed in the art are measuring devices that can be integrated with existing tools and in one particular embodiment, with medical tools.

SUMMARY

According to one embodiment, disclosed is a medical tool that includes a distance guide. For instance, the medical tool can include a first arm and a second arm that are attached to one another at a pivot point. Each arm includes a jaw in mechanical communication with the respective arm, for instance at an end of the arm. Relative motion between the arms via rotation at the pivot point causes the jaws to move from a first position to a second position. The distance guide of the tool extends along at least a portion of the length of one of the arms.

Also disclosed is a measuring device that includes a first edge and a second edge. The first edge includes an attachment that can be used to attach the measuring device to a tool that includes a pair of jaws, the jaws being capable of moving with respect to one another from a first position to a second position. For example, in one embodiment the device can be attachable to a medical tool such as a hemostat. The measuring device includes a distance guide along or near the second edge. The measuring device is attachable to the tool such that one component of the tool (e.g., an arm) moves past the second edge as the jaws move from the first position to the second position. For example, the second edge can form an arc and the arm can move past the second edge as the jaws of the tool are opened and closed. There is an alignment between the tool component and the distance markings of the measuring device that can indicate the distance between the jaws. In one embodiment, the device can be utilized to measure the size of an object gripped by the jaws, for instance the size of an object that can be manipulated by the jaws.

BRIEF DESCRIPTION OF THE FIGURES

A full and enabling disclosure of the present invention, including the best mode thereof, directed to one of ordinary skill in the art, is set forth in the specification, which makes reference to the appended figures, in which:

FIG. 16 illustrates a distance guide including a sliding attachment clamp.

FIG. 17 illustrates a side view of the distance guide of FIG. 16.

FIG. 18 illustrates a side view of the attachment clamp of FIG. 16.

FIG. 19 illustrates a tool arm including a channel for the attachment clamp of FIG. 16.

FIG. 20 illustrates a method for attaching the distance guide of FIG. 16 to the channeled arm of FIG. 19.

Figure 1:
FIG. 1 is an x-ray image of a foreign object in a patient's foot.
Figure 2:
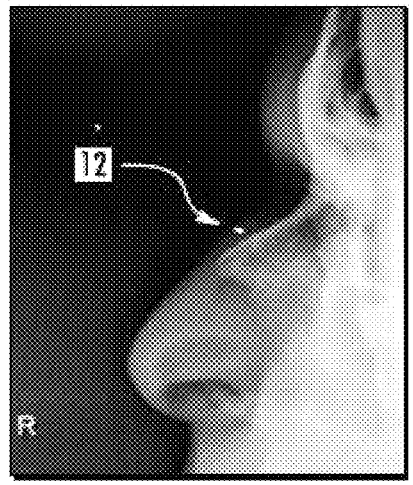
FIG. 2 is an x-ray image of a foreign object in a patient's nose.
Figure 3A:
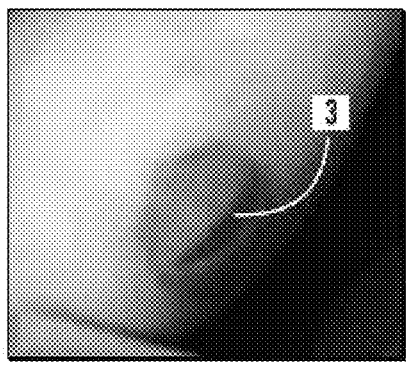
FIG. 3A is an image of a facial laceration before suturing.
Figure 3B:
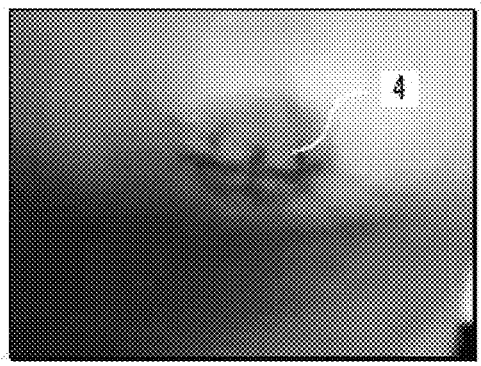
FIG. 3B is an image of a facial laceration after suturing.
Figure 4:
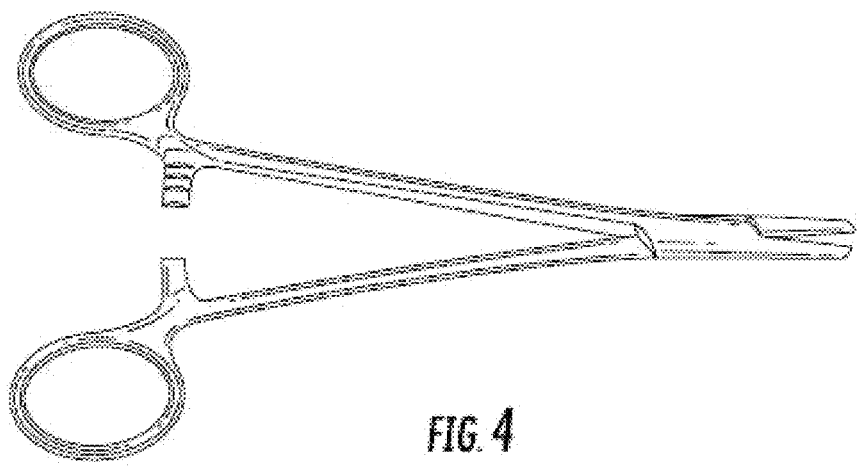
FIG. 4 illustrates a common hemostat.

Repeat use of reference characters throughout the present specification and appended drawings is intended to represent same or analogous features or elements of the invention.

DETAILED DESCRIPTION

Reference now will be made in detail to embodiments of the disclosed subject matter, one or more examples of which are illustrated in the drawings. Each example is provided by way of explanation of the subject matter, not limitation thereof. In fact, it will be apparent to those skilled in the art that various modifications and variations can be made to the presently disclosed subject matter without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

The present disclosure is generally directed to measuring devices that can be incorporated with gripping tools. The measuring devices can be integral to a gripping tool or can be removably attachable to a gripping tool. In one embodiment, the measuring devices can be beneficially incorporated in conjunction with a gripping tool for use in a medical application. For instance, the measuring devices can be particularly beneficial when incorporated and utilized with a medical tool such as a clamp, a hemostat, a forceps, or the like. However, it should be understood that while the following description is primarily directed to the utilization of the measuring devices in conjunction with a medical tool such as a hemostat, the description is in no way limited to use in a medical application, and the disclosed devices are also encompassed for use with gripping tools in non-medical applications. In addition, medical tools encompassed herein include, but are not limited to examination, procedural, and surgical tools for medical, dental, and/or veterinary use. Gripping tools as encompassed herein are generally hand tools of a size to be manipulated and provide suitable leverage when utilized by an average adult. For instance, the gripping tool can have an overall length of from about 3.5 inches to about 10 inches, or about 6 inches on some embodiments.

The measuring devices (synonymously referred to a distance guides throughout this description) can be utilized in determining the size of an object as well as distances associated with the location and/or placement of an object. For instance, when considering the removal of a partially or completely embedded foreign object from a subject in need thereof, the distance guides can be utilized to determine not only the dimensions of the foreign object, but also the embedded depth of the foreign object, the size of a wound associated with the foreign object, and so forth.

Beneficially, the distance guides can be utilized for in situ determination of dimensions in medical applications. For example, the dimensions and depth of an internally located foreign object can be determined in situ prior to removal. Similarly, the dimensions of a wound can be determined prior to or during treatment. This information can be utilized to confirm proper care. When considering an embedded foreign object, this information can be utilized to confirm that the entire object was removed following an ex vivo measurement following removal. The information provided by the distance guides can also be utilized for reporting requirements, for instance for insurance remuneration requirements. Beneficially, the distance guides are a permanent or removably attachable component of a gripping tool, and as such can provide useful information without the necessity of a separate tool that would otherwise need to be associated with the procedure.

Figure 5A:
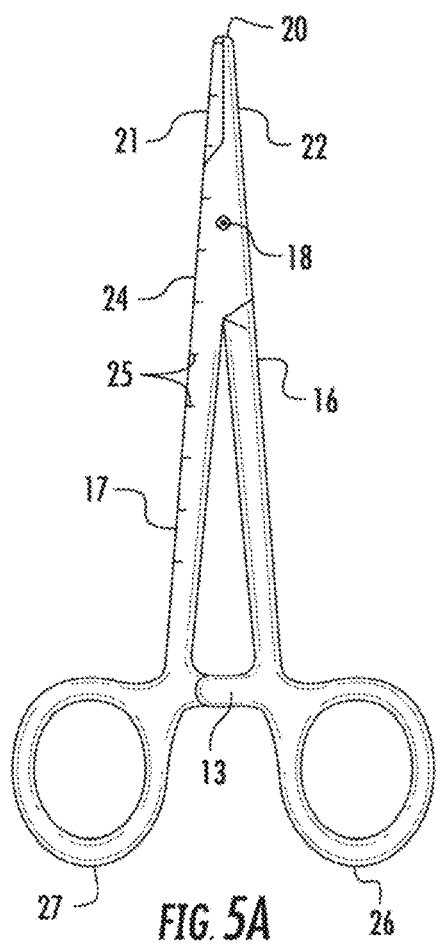
FIG. 5A illustrates a hemostat including a distance guide along one side thereof in a closed position.
Figure 5B:
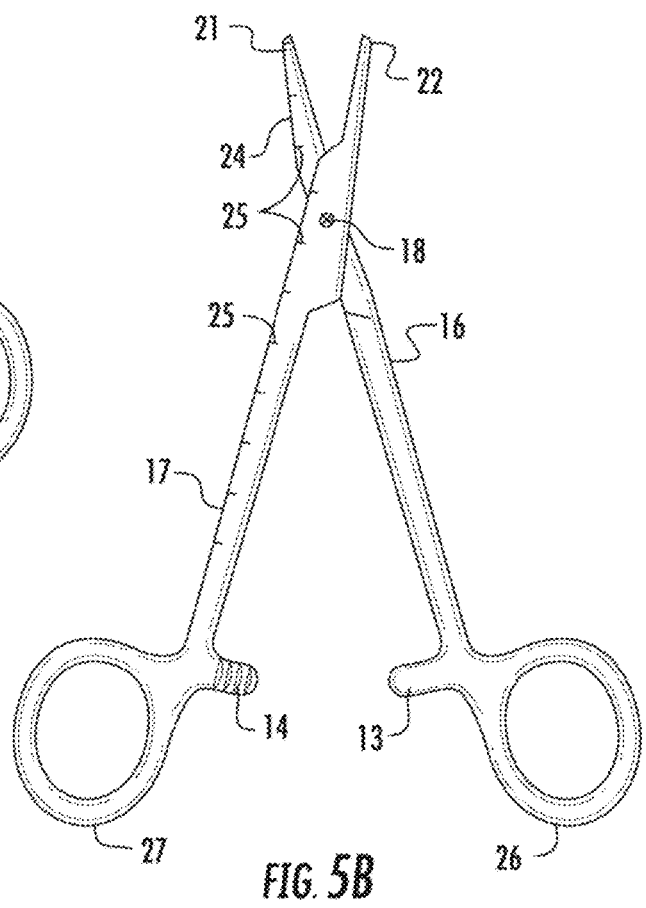
FIG. 5B illustrates a hemostat including a distance guide along one side thereof in an open position.

FIG. 5 illustrates a hemostat in a closed configuration (FIG. 5A) and in an open configuration (FIG. 5B). The hemostat includes standard features including a pair of jaws formed from a first jaw 21 and a second jaw 22. As shown, the jaws 21, 22 are at the termini of the two arms 16, 17 that form the hemostats. Specifically, the jaw 21 is the terminal portion of the arm 16 and the jaw 22 is the terminal portion of the arm 17. The two arms 16, 17 are joined to one another at a pivot point 18 such that the two arms 16, 17 can rotate with respect to one another and the arms can move from a closed position (as in FIG. 5A) to an open position (as in FIG. 5B).

The hemostat of FIG. 5A and FIG. 5B include single arms 16, 17 that extend straight along the entire length of the hemostat from the rings 26, 27 to the tip 20 at the terminus of the jaws 21, 22. As such, when the rings 26, 27 are separated, the jaws 21, 22 will be open (FIG. 5B). Of course, other geometric arrangements are encompassed herein, for instance, a tool in which one or both of the arms are hinged, bent, or angled. For example, one arm can be bent such that when the rings are open the jaws are closed. In any case, rotational motion of the arms with respect to one another via a pivot point will cause the jaws to move in order to open and close the jaws. The materials used to form the gripping tool can be those as generally known in the art including, without limitation, stainless steel, hardened steel, nickel alloys, etc. In one embodiment, the jaws 21, 22 can include a permanent magnetic material, which can aid in gripping certain objects. Similarly, the handles can include a coating, for instance an elastomeric covering that can aid in gripping the tool.

The hemostat of FIG. 5A and FIG. 5B includes rings 26, 27 as handles. Of course, any suitable handle type is encompassed for a gripping tool that incorporates a measuring device as disclosed herein. In addition, the hemostat of FIG. 5A and FIG. 5B includes ratcheted interlocks 13, 14 that interlock with one another to lock the hemostat in a closed position, as is known in the art.

The hemostat of FIG. 5A and FIG. 5B includes a distance guide 24 formed to include a series of distance markings 25 that extend along one side of the length of the arms 16, 17. In this embodiment, the distance guide 24 begins at or near the tip 20 of the device, extends along a portion of one arm 16 and continues along a portion of the second arm 17. Thus, when the hemostat is closed as shown in FIG. 5A, the distance guide extends along both arms in a single length, and when the hemostat is open as shown in FIG. 5B the distance guide has a break in the middle in conjunction with the pivot point 18. Alternatively, a distance guide can extend along only one arm, for instance along a portion of an arm that is distal to the pivot point.

The distance guide can be of a length to be useful in measuring wounds, objects, etc. as may be encountered in a gripping application. For instance, the distance guide can be about 1 inch (about 2.5 centimeters) or longer, about 1.5 inches (about 3.5 centimeters) or longer, or about 2 inches (about 5 centimeters) or longer in some embodiments. In one embodiment, the distance guide can be from about 2.5 centimeters to about 15 centimeters or from about 2.5 centimeters to about 10 centimeters in some embodiments.

The markings for the distance guide can be presented in any desired graduated length dimensions, such as centimeters, millimeters, inches, or combinations thereof. In one embodiment, a tool can include multiple distance guides, for instance a first distance guide along a first side of the tool (e.g., along a portion of arm 17 near the jaw 21 and along a portion of arm 16 between the pivot point 18 and the ring 27) and a second distance guide along a second, opposite side of the tool (along a portion of arm 16 near the jaw 22 and along a portion of arm 17 between the pivot point 18 and the ring 26). The first distance guide can present the distance markings in one length dimension (e.g., centimeters) and the second distance guide can present the distance markings in another length dimension (e.g., inches). Alternatively, both distance guides can present one or more identical distance markings. The presence of multiple distance guides on a single device can provide for ease of use as well as provide the required reporting information in any necessary dimensions.

The distance guide can be formed into the material of the tool or can be applied to the formed tool, as desired. For instance, in one embodiment, the arms of the medical tool can be formed of a typical tool metal or metal alloy, e.g., stainless steel, and the distance markers of the distance guide can be engraved in the metal that forms the arms at the proper locations. Alternatively, the distance guide can be applied to the arms following formation. For instance, the individual distance markers can be printed or otherwise applied to the arms in the proper locations. Alternatively, a portion of the distance guide including multiple distance markers can be applied to the arm at a single time. For example, one or more adhesive strips printed with a plurality of distance markers can be adhered to the arm(s) in the proper locations to form the complete distance guide.

The arm that carries a distance guide can likewise be of any suitable cross sectional shape. For instance, the section of the arm that carries a distance guide (or portion thereof) can include a relatively flat surface along which the distance guide extends. The remainder of the arm can have a similar cross section or can vary. For example, the distance guide portion can be relatively flat, while another section of the arm can be more rounded in cross section, can include surface features for improve grip or can otherwise be varied in cross sectional geometry for any aesthetic or functional purpose.

Figure 6:
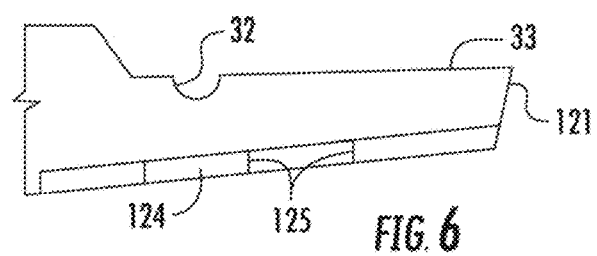
FIG. 6 illustrates a tool jaw including an end gripping area and a gripping notch on the inner surface of the jaw; and also including a portion of a distance guide on an outer surface of the jaw.

A tool can include additional components that can be useful in medical applications. For example, FIG. 6 illustrates a jaw 121 that includes a series of distance markings 125 as a portion of a distance guide 124. In addition, the jaw 121 includes a gripping notch 32 that is distal to the gripping surface 33. The gripping notch 32 can improve grip for grasping and manipulating an object having a relatively small cross sectional area.

Figure 7:
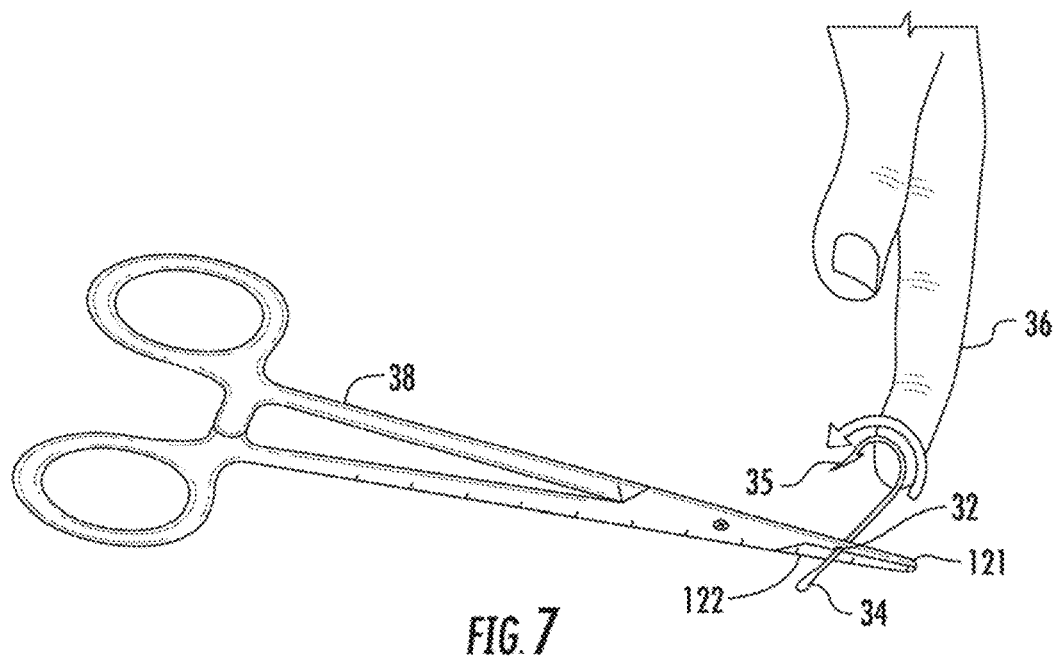
FIG. 7 illustrates a method for utilizing a gripping notch of a medical device for removal of a foreign object from an individual's finger.

By way of example, FIG. 7 illustrates the manipulation of a fish hook 34 that has been embedded in a human finger 36. A hemostat 38 that includes a gripping notch 32 can be used to grasp the shaft of the fish hook 34 between the gripping notch 23 of the jaw 121 and the mated jaw 122. The mated jaw 122 can also define a gripping notch or can mate the gripping notch 32 with a relatively flat gripping surface.

To remove the embedded fish hook 34, it is necessary for medical personnel to push the embedded hook through the patient's body part, e.g., the finger 36 until the barb 35 exits the skin as demonstrated by the directional arrow in FIG. 7. At this point, the barb 35 can be cut off of the hook 34 and the now barb-less hook can be pulled back out of the finger 36 along the entry path. The first step of the removal process, pushing the hook through the patient's finger 36 until the barb 35 is forced out of the body, requires manipulation of the hook preferably via the shortest route possible. The size and shape of the hook can make it difficult to properly grasp and manipulate the hook with the necessary rotational motion.

The gripping notch 32 of a grasping tool such as hemostat 38 can improve grip of the tool on a small item such as a fish hook and improve the ability to apply the necessary torque to rotate the embedded item as desired. A gripping notch can be utilized to improve grip on any object having a relatively small diameter including, without limitation, fish hooks, earrings, rings, piercings, nails, screws, wires, etc.

A gripping notch can have a surface that is the same or different as the gripping surface of a jaw or any other portion of a gripping tool. For instance, a gripping notch can have a surface formed of the same material as the gripping surface of a jaw (e.g., a metal or metal alloy) and the surface can be smooth or roughened. In one embodiment, a gripping notch can include a coating or a thicker material applied to the base material that can alter the surface characteristics of the gripping notch. For instance, a gripping notch can include a surface materials such as an elastomeric or the like that can alter the surface characteristics of the gripping notch and improve gripping characteristics of the gripping notch.

Figure 8:
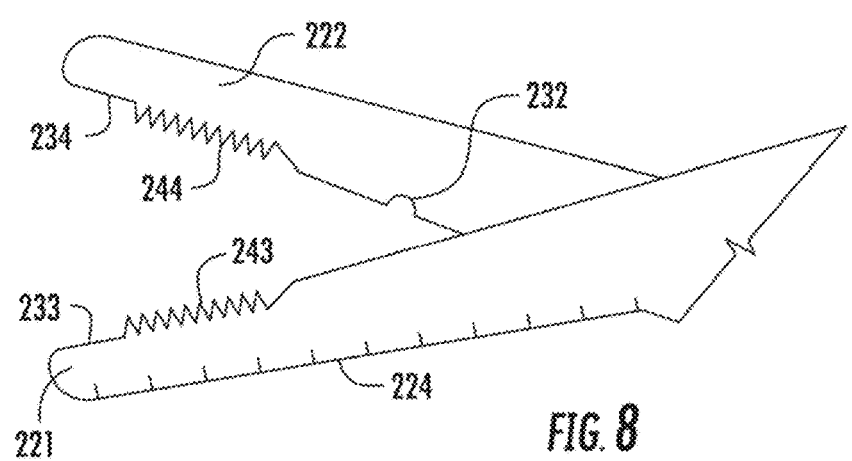
FIG. 8 illustrates a pair of jaws including a first gripping area and a second gripping area on a first side of both jaws, a gripping notch on one of the jaws, and a portion of a distance guide on an outer surface of one of the jaws.

A gripping notch can be located at any convenient location on a tool. For example, in the embodiment of FIG. 6, the gripping notch 32 is immediately distal to the gripping surface 33 of the jaw 31. FIG. 8 illustrates another embodiment of jaws 221, 222 of a gripping tool. As shown, the jaws 221, 222 each include a first gripping surface 233, 234 at the end of the jaws 221, 222, respectively. One jaw 222 also includes a gripping notch 232. The other jaw 221 does not include a gripping notch. Thus, in this embodiment, when an object is gripped by use of the gripping notch 232, the object will be held between the surface of the gripping notch 232 and the relatively flat surface of the mated jaw 221. In another embodiment, both of the jaws can include gripping notches that meet upon closure of the jaws, for instance, when the tool is designed to hold relatively larger objects.

The jaws 221, 222 of FIG. 8 include additional a distance guide 224 along an outer surface of jaw 221. Jaws 221, 222 also include additional gripping areas formed to have gripping capabilities that differ from the first gripping surfaces 233, 234. Specifically, jaws 221, 222 include gripping surfaces 243, 244, respectively, which have a higher surface area causing a roughened surface that can alter the gripping characteristics between the jaws at gripping surfaces 243, 244. The roughened section can be, for example, a series of serrations or teeth formed into the gripping surfaces 243, 244 of the jaws 221, 222.

Figure 9:
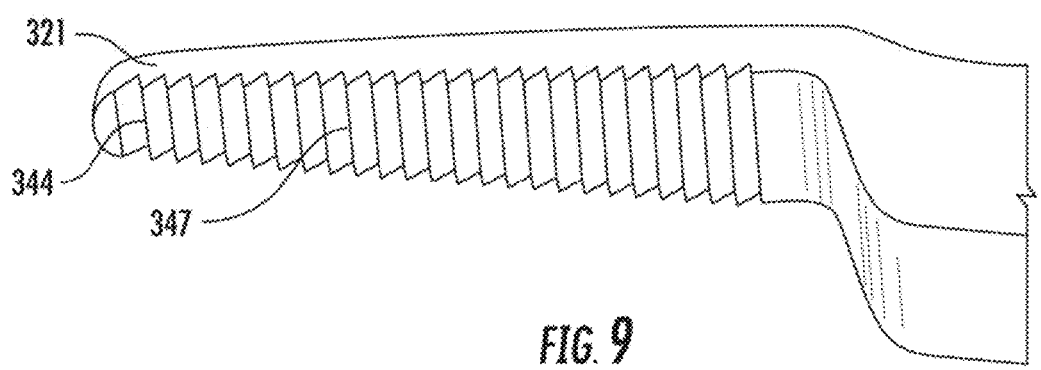
FIG. 9 illustrates one example of a roughened gripping surface as may be incorporated in a tool.

One example of a high surface area roughened gripping surface is illustrated on the gripping surface 344 of the jaw 321 illustrated in FIG. 9. As can be seen, the gripping surface 344 includes a series of serrations or teeth formed into the metal that forms the jaw 321. The jaw also includes a channel 347 that runs generally down the center of the gripping surface 344 for fluids that may be present in the area to be gripped by the jaw 321. As shown in this embodiment, the roughened gripping surface 344 section extends along the entire length of the gripping surface of the jaw, which may be preferred in some embodiments.

The entire gripping surface of a jaw can have the same surface characteristics such as the relatively smooth gripping surface 33 of FIG. 6 or the rougher gripping surface 344 of FIG. 9. Optionally, a jaw 221 can include multiple gripping sections 233, 243 having different roughness levels as in FIG. 8. Multiple gripping surfaces on a single tool can provide multiple levels of gripping capability that can preferentially be utilized depending upon exactly what material is to be gripped between the jaws and what level of force is appropriate. For instance, it may be inappropriate to utilize a roughened gripping surface on human tissue, as the force level could damage the tissue. In another embodiment, a roughened gripping surface may be preferred in order to properly grip and manipulate an embedded object, such as the smooth round metal shaft of a fish hook or a piece of jewelry.

Figure 10:
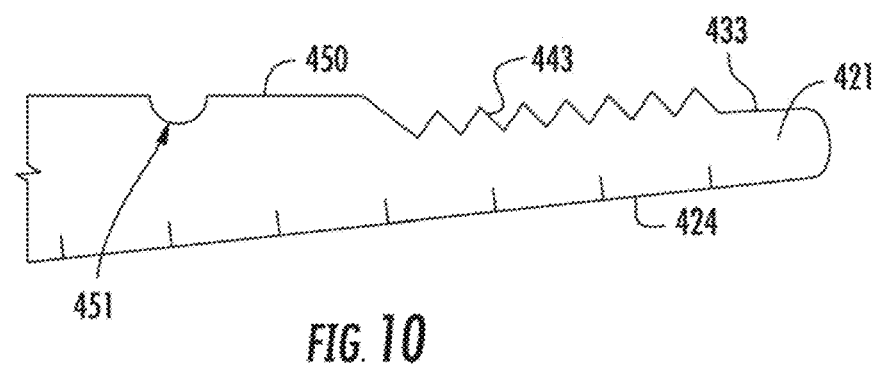
FIG. 10 illustrates a jaw including a first gripping area, a second gripping area, a cutting blade, and a cutting notch on one side of the jaw and a portion of a distance guide on another side of the jaw.

FIG. 10 illustrates another jaw 421 including a distance guide 424 on one side of the jaw 421. The gripping side of the jaw 421 includes multiple features that may be of benefit during u se including a first gripping surface 433 at the end of the jaw 421 and a second gripping surface 443 distal to the first gripping surface 433. The second gripping surface 443 has a roughened surface to provide for an increased grip when desired. The jaw 421 also includes cutting edges that can be used for cutting, without limitation, human or animal tissues, foreign objects embedded in a patient, medical materials (suture, gauze, etc.), and so forth. A first cutting edge 450 is a scissor-type straight blade that can have a mated cutting edge on the second jaw of the gripping tool. This cutting edge 450 can be utilized for cutting relatively thin materials such as gauze, suture, etc.

A tool can also include a cutting notch 451 that can be utilized to cut larger materials. The cutting notch 451 can be mated with a flat cutting blade on the second jaw or may be mated with another cutting notch, as desired. A cutting notch 451 can include a sharp cutting edge and be of a size to cut objects such as jewelry posts, fish hooks, etc.

A tool can include a gripping surface and a distance guide optionally in combination with one or more additional components including but not limited to the components described herein in any combination. For instance, a tool can include both types of cutting edges (a straight-edge blade and a cutting notch), can include only one cutting edge or, may not include a cutting edge at all. Similarly, a tool can include multiple different types of gripping surfaces or only a single gripping surface and/or can include a gripping notch on the jaws and any of these options may be combined with one or more cutting edges.

Figure 11:
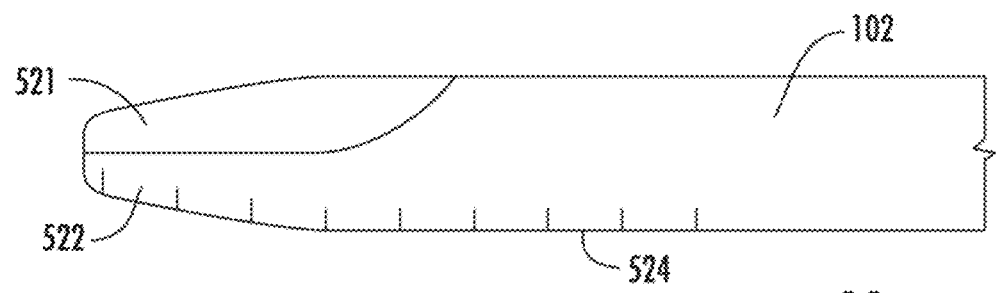
FIG. 11 illustrates one embodiment of an ornamental profile of a gripping tool.
Figure 12:
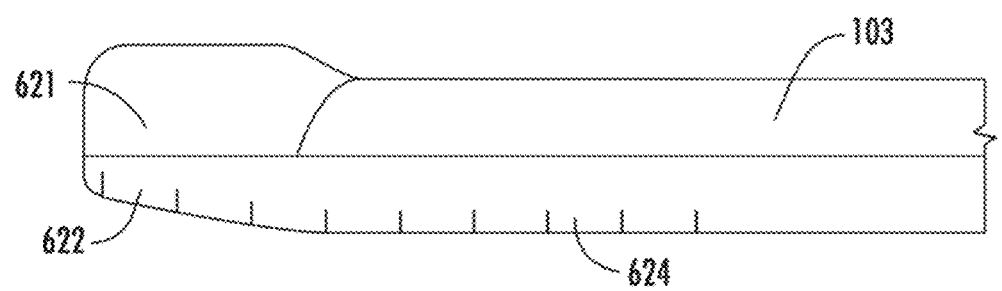
FIG. 12 illustrates another embodiment of an ornamental profile of a gripping tool.

A tool can also include ornamental aspects. For instance, the profile of a gripping tool can be designed with a recognizable ornamental design. By way of example, FIG. 11 and FIG. 12 present two alternative ornamental designs for a tool profile. In these embodiments, the tools 102, 103 have been designed such that in profile the jaws 521, 522 and the jaws 621, 622, resemble the profile of a humpback whale and a sperm whale, respectively when closed. As can be seen, the gripping tool 102 includes a distance guide 524 along a length of jaw 522 and gripping tool 103 includes a distance guide 624 along a length of jaw 622.

Figure 13A:
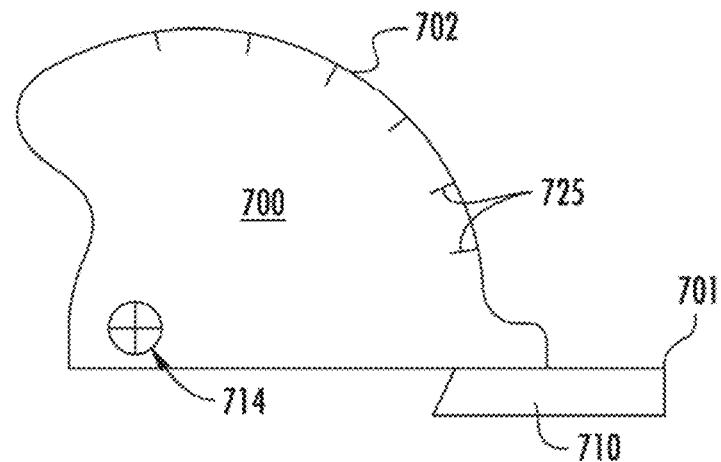
FIG. 13A is a front view of a distance guide for use in measuring the distance between the jaws of a tool.
Figure 13B:
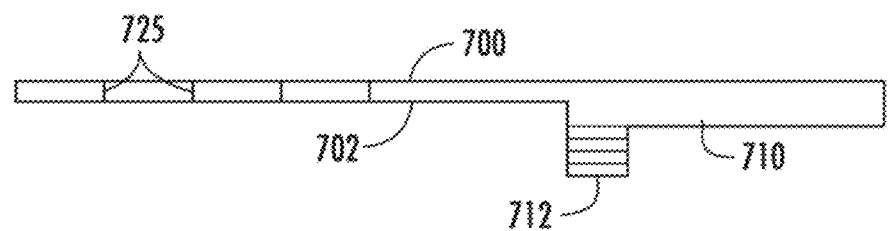
FIG. 13B is a top view of a distance guide for use in measuring the distance between the jaws of a tool.
Figure 13C:
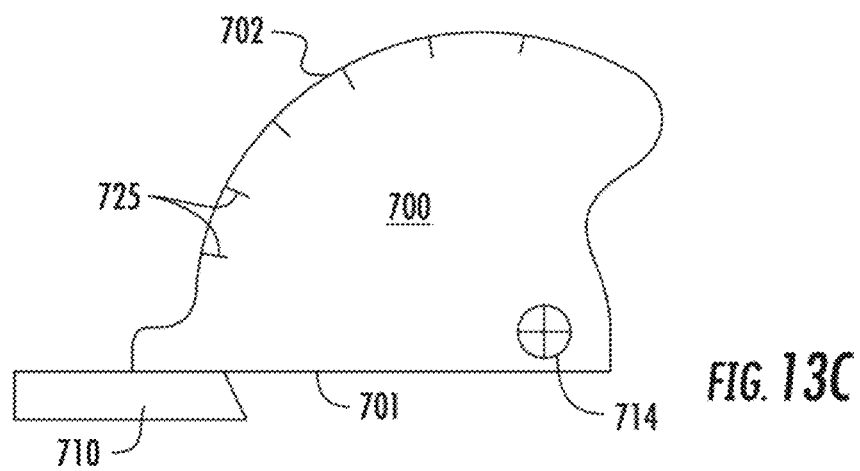
FIG. 13C is a back view of a distance guide for use in measuring the distance between the jaws of a tool.

Another measuring device 700 for use in conjunction with a gripping tool is illustrated in FIG. 13 including a front view (FIG. 13A), a top view (FIG. 13B) and a back view (FIG. 13C). This type of measuring device can be utilized to determine the distance between the jaws of a gripping tool. In one embodiment, the measuring device 700 can be removably attachable to a gripping tool and thus can be attached when a measurement is desired and removed for those applications in which no jaw width measurement is necessary. This is not a requirement, however, and in other applications a measuring device 700 can be a permanent feature of a gripping tool.

A measuring device for determining the distance between the jaws of a gripping tool can be utilized in conjunction with a gripping tool as described herein. For instance, the measuring device 700 can be utilized in conjunction with a gripping tool that includes a distance guide as described previously as well as with one or more other optional components including but not limited to components as described herein such as one or more gripping notches, multiple gripping surfaces, one or more cutting edges, and so forth.

A measuring device can have an ornamental shape for aesthetic or recognition purposes. For instance, the measuring device 700 has a profile similar to the snout of a whale, though any other design is encompassed herein.

The measuring device 700 includes a first edge 701 and a second edge 702. The second edge 702 includes a series of distance markings 725 that are distributed along at least a portion of the length of the second edge 702. In the embodiment of FIG. 12, the distance markings can be seen on the front (FIG. 13A), top (FIG. 13B) and back (FIG. 13C) of the device 700. In other embodiments, the distance markings may be located on only one or two of these surfaces. In addition, the distance markings need not extend to the edge of any one surface, but will generally be near the second edge 702 of the device, so as to be more readily visible and provide maximum distance between adjacent distance markings 725. In general, the second edge 702 can be curved to mirror the rotational motion of the gripping tool, but this is not a requirement of the measuring device 700.

When included on multiple sides of the device 700, the distance markings can be the same dimension or different. For instance, the distance markings on the front of the device can be in millimeters, and the distance markings on the back of the device can be in inches. Multiple dimensions can also be included on a single side of the device.

The measuring device 700 also includes an attachment mechanism 710 that can be utilized to attach the device 700 to a gripping tool. For instance, the attachment mechanism 710 can include a peg 712 designed to snap into a mated hole on a gripping tool.

The measuring device 700 can include any suitable sort of one or more attachment mechanisms to secure the device to a gripping tool. For instance, the device 700 can include a second attachment mechanism 714 that can aid in securing the device 700 to a gripping tool and/or to align the gripping tool with the device 700. For instance, attachment mechanism 714 can be designed to align with the pivot point of a gripping tool to insure proper alignment between the device and the gripping tool.

Figure 14:
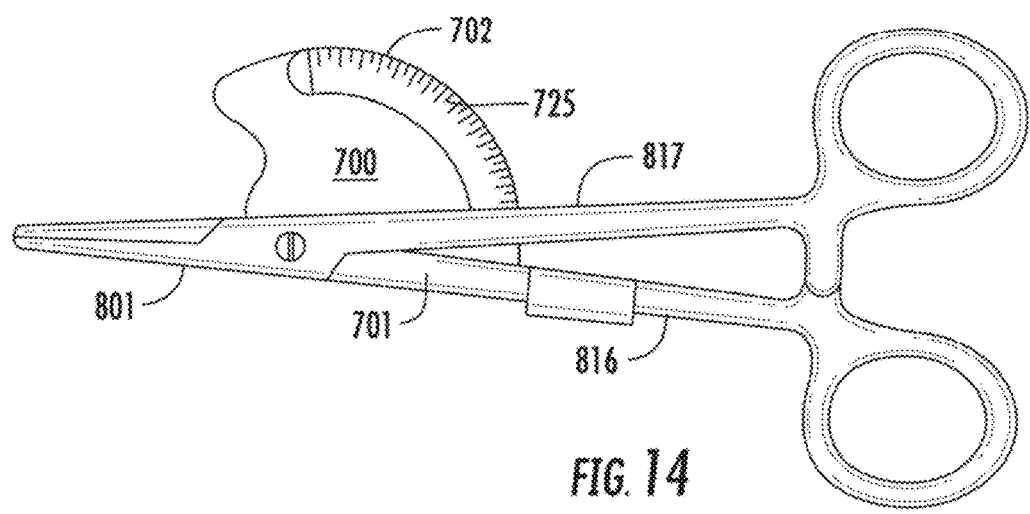
FIG. 14 illustrates a hemostat attached to a distance guide for use in measuring the distance between the jaws of a tool.

FIG. 14 illustrates a gripping tool 801 including a measuring device 700 attached thereto. As can be seen, the first edge 701 has been attached to the arm 816 of the gripping tool and the second edge 702 extends past the arm 817 with the distance markings 725 thereon.

Figure 15:
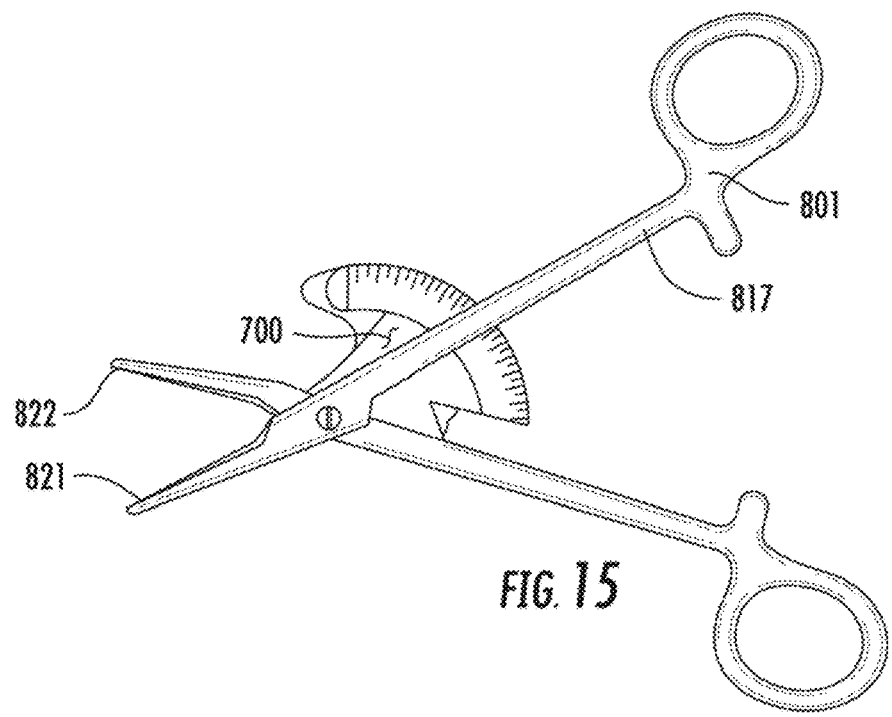
FIG. 15 illustrates the hemostat of FIG. 14 with the jaws open.

FIG. 15 illustrates the gripping tool 801 with the jaws 821, 822 open. Upon separating the jaws 821, 822 from one another, the arm 817 will move past the distance markings 725. The distance markings 725 can be correlated with the distance between the jaws 821, 822 such that by simply reading the distance marking closest to the alignment location of the arm 817, a user can determine the width between the jaws 821, 822.

The alignment location can generally be marked on the arm 817. For instance, the arm 817 can be marked on the top or the bottom side to provide a user with the proper alignment location for reading the distance marking of the distance guide. In addition, the jaw width that is correlated with the distance markings can in one embodiment be that at the termini of the jaws, though this is not a requirement of the system.

The measuring device 700 can provide the distance between the jaws 821, 822 in one or more suitable dimensions including, without limitation, millimeters, centimeters, and/or inches. For instance, a first distance guide present on one surface of a measuring device 700 can provide the distance markings in centimeters and a second distance guide on another surface of the measuring device can provide distance markings inches, tenths of inches, etc. Of course, a single distance guide can include multiple different dimensional markings.

To accurately determine the distance between two jaws, a measuring device must be properly located on a gripping tool. FIG. 16 illustrates a measuring device 900 including a sliding locking clamp 850. FIG. 17 presents a side view of the measuring device 900 and FIG. 18 presents a side view of the clamp 850. The clamp includes a hole 851 designed to mate with a peg 852 of the measuring device 900. In addition, the clamp 850 includes a peg 853 designed to mate with a channel 854 of a tool arm 916 (FIG. 19).

The peg 853 of the clamp 850 is a portion of a flexible arm 855 that can be utilized to unlock the clamp 850 from the tool arm 916 as described further herein.

As can be seen in FIG. 18, the clamp 850 can have an overall width so as to fit over both the measuring device 900 and the arm 916 of a gripping tool at the lower edge 901 of the measuring device and the lower edge 918 of the arm 916. Specifically upon aligning the measuring device 900 with the arm 916 of the tool, a portion of the bottom edges of both the measuring device 900 and the arm 916 will be nested in the clamp 850.

Upon alignment of the measuring device 900 with the arm 916 of the gripping tool, the clamp can be used to slidably engage the channel 854 and lock the measuring device 900 to the tool arm 916. For instance, the measuring device 900 can include one or more alignment components 814 that can optionally provide another attachment point between the measuring device and a gripping tool. In one embodiment, an alignment component can be located in conjunction with the pivot point of a gripping tool to insure proper alignment.

FIG. 20 illustrates a method of attaching the clamp 850 to a gripping tool. Following proper alignment, the clamp 850 can be slid across the measuring device as designated by the direction arrow in FIG. 20. As the peg 853 slides off of the surface of the measuring device 900 it will drop into the channel 854 of the arm 916. In addition, the hole 851 will be slid toward the mated peg 852.

Figure 21:
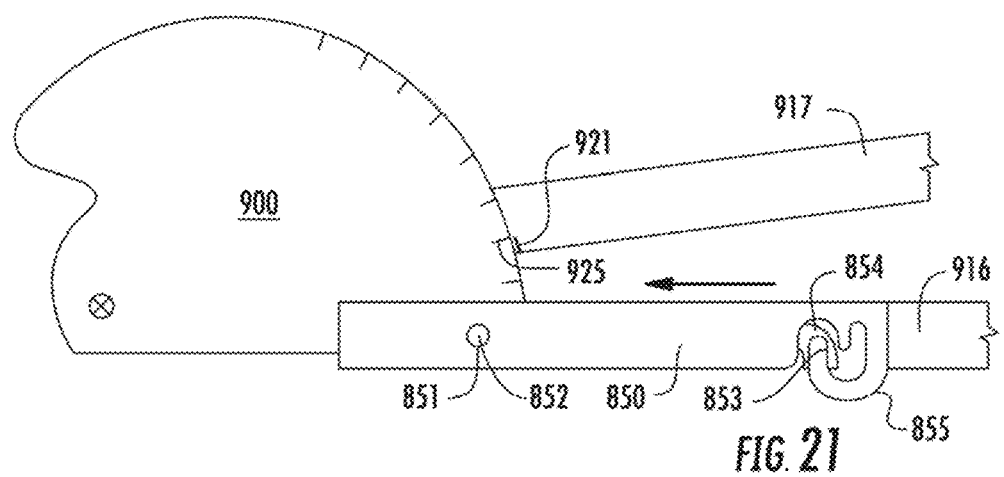
FIG. 21 illustrates the distance guide of FIG. 16 following attachment to the arm of FIG. 19.

FIG. 21 presents the measuring device 900 upon attachment to the arm 916. As illustrated, the peg 852 is seated in the hole 851 and the peg 853 has dropped into the end portion of the channel 854. The arm 917 can include a mark 921 that can provide a user with the proper alignment location for reading the closest distance marker 925, which correlates to the width between the jaws of the gripping tool.

To remove the measuring device 900 from the arm 916 following use, the flexible arm 855 can be pushed upward to move the peg 853 up to the horizontal section of the channel 854. At the same time, force can be applied to the clamp 850 in the direction of the directional arrow of FIG. 21, which can force the peg 852 out of the hole 851 and slide the peg 853 back along the channel 854.

It should be understood that an attachment device or mechanism can engage both sides of an arm of a gripping tool, and is not limited to a single side attachment as is illustrated in the embodiment of FIG. 16-FIG. 21. In addition, any suitable attachment mechanism can be utilized to properly align and attach a measuring device to a gripping tool.

Figure 22A:
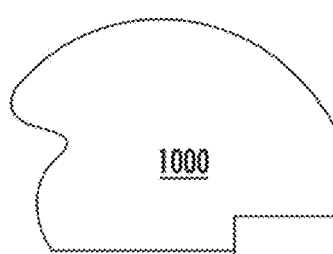
FIG. 22A illustrates a front view of a distance guide including another attachment mechanism.
Figure 22C:
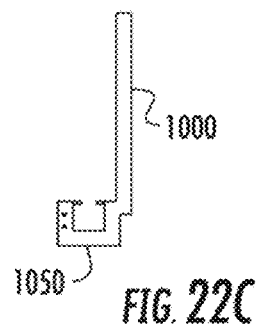
FIG. 22C illustrates an end view of a distance guide including another attachment mechanism.
Figure 22B:
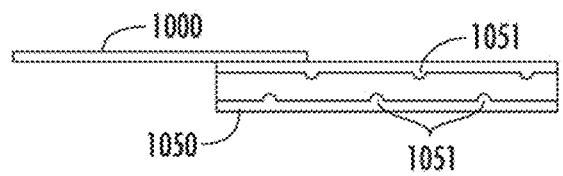
FIG. 22B illustrates a top view of a distance guide including another attachment mechanism.

FIG. 22 presents another embodiment of a measuring device 1000 including a clamping attachment mechanism as may be utilized to attach a measuring device to a gripping tool. In this embodiment, the measuring device includes a clamp 1050 attached thereto. FIG. 22A illustrates the device in a front view, FIG. 22B illustrates the device in a top view, and FIG. 22C illustrates the device in an end view.

The clamp 1050 is of a cross sectional size and shape such that the arm of a gripping tool can be set within the clamp (FIG. 22B). The clamp 1050 also includes a series of teeth 1051 of a size and shape to snap over the top of the tool arm following insertion of the arm into the clamp and secure the clamp to the arm. In addition, the clamp defines a slot 1052 in the front side of the clamp 1050.

Figure 23A:
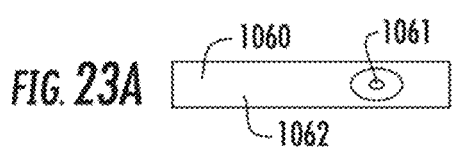
FIG. 23A illustrates a front view of a locking tab for use with the distance guide of FIG. 22.
Figure 23C:
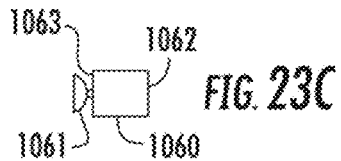
FIG. 23C illustrates an end view of a locking tab for use with the distance guide of FIG. 22.
Figure 23B:
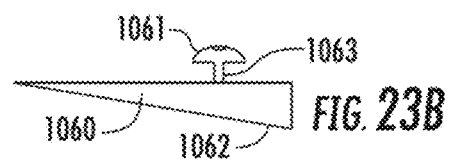
FIG. 23B illustrates a top view of a locking tab for use with the distance guide of FIG. 22.

FIG. 23 illustrates a locking slide 1060 designed to be held in the slot 1052 of the clamp 1050. FIG. 23A presents a front view of the locking slide 1060, FIG. 23B presents a top view of the locking slide 1060, and FIG. 23C presents an end view of the locking slide 1060.

The locking slide 1060 includes a tab 1061 and a body 1062 adjoined to one another via a neck 1063. The body 1062 has a tapered length, as shown. The locking slide will be attached to the clamp 1050 such that the tab 1061 extends from the front of the clamp 1051, the neck 1063 is within the slot 1052 of the clamp and the body 1062 in on the interior of the clamp 1050 (see FIG. 25). Thus, the locking slide can be moved via the external tab 1061 to slide within the clamp 1050 with the body 1062 of the locking slide 1060 within the clamp 1050.

Figure 24:
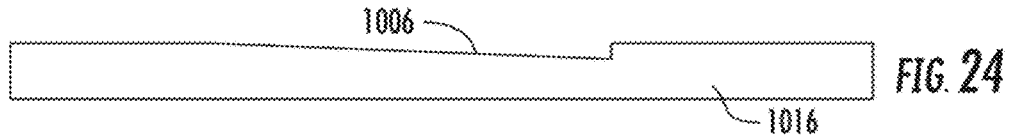
FIG. 24 illustrates a tool arm for use with the attachment mechanism of FIGS. 22 and 23.

FIG. 24 illustrates a top view of a tool arm 1016 that can be connected to the device of FIG. 22. As shown, the arm 1016 also has a tapered section 1006 that will be in the opposite direction of the taper of the locking slide 1060. Thus, the tapered length of the locking slide 1060 can set into the tapered length 1006 of the arm 1016.

Figure 25A:
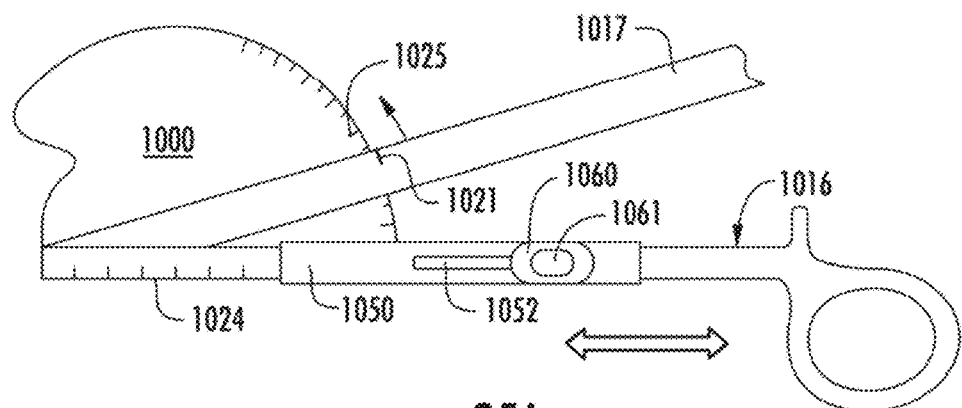
FIG. 25A illustrates a front view of the distance guide of FIG. 22 following attachment to a gripping tool.
Figure 25B:
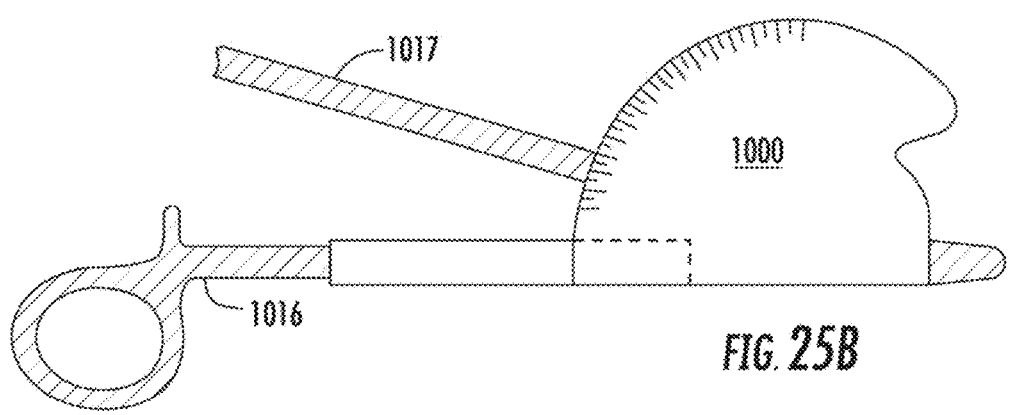
FIG. 25B illustrates a back view of the distance guide of FIG. 22 following attachment to a gripping tool.
Figure 25C:
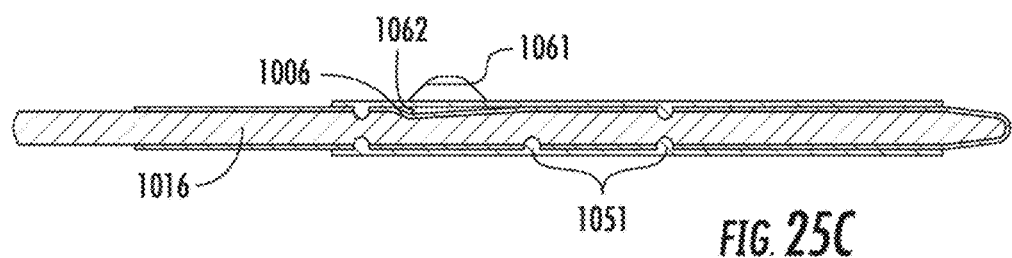
FIG. 25C illustrates a top view of the distance guide of FIG. 22 following attachment to a gripping tool.

FIG. 25 illustrates the measuring device 1000 following attachment to a gripping tool including arm 1016 and arm 1017 including a front view (FIG. 25A), a back view (FIG. 25B), and a top view (FIG. 25C). As shown, the locking slide 1060 is attached to the clamp 1050 via the slot 1052 such that the tab 1061 extends from the front of the clamp 1050 and the tapered body 1062 is within the clamp and adjacent to the tapered portion 1006 of the arm 1016. Thus, by aligning the locking slide 1060 with the tapered portion 1006, a user can be assured of properly aligning the measuring device 1000 with the gripping tool and thus be assured of accurate measurements of the jaw width.

The locking slide 1060 can slide within the slot 1052 as indicated by the directional arrow in FIG. 25A. By sliding the locking slide 1060 within the slot 1052, the tapered body 1062 can push against the tapered section 1006 of the arm 1016 and provide a tight friction fit between the two. In some embodiments, following use, the locking slide 1060 can be further forced to slide beyond the point of a friction fit with the arm 1016, and can pop the teeth 1051 of the clamp 1050 off of the arm 1016 for separation of the measuring device 1000 from the gripping tool.

Though not illustrated in the figures, a device can include a similar or different alignment mechanism on the back of the clamp 1050 and arm 1016. For instance, the inner wall of the clamp 1050 can define a tapered surface, a peg, a notch, etc. that can be mated with the inverse shape on the back side of the arm 1016 for alignment between the two.

During use, as the arms 1016, 1017 move in relation to one another, the measuring device 1000 can be utilized to determine the distance between the jaws of the tool (not shown in FIG. 25). For instance, as the upper arm 1017 moves in the direction as indicated by the directional arrow of FIG. 25A, an indicator mark 1021 can be aligned with a distance mark 1025 of the measuring device to indicate the jaw width. As previously mentioned, the measuring device can include multiple dimensions, for instance millimeters can be indicated by the distance markings on the front of the device and inches can be indicated by the distance markings on the back of the device.

The non-attachment arm 1017 can be shaped to improve alignment with the distance guide. For instance, the non-attachment arm 1017 can include a flat surface at least along that portion of the arm 1017 that will be adjacent to the front surface of the measuring device 1000 during use, such that the flat portion will slide past the measuring device. The remainder of the back side of the arm 1017 can likewise have a flat surface or can be more rounded, as desired.

As mentioned previously, measuring devices as disclosed herein can include both the jaw-measuring device and the straight edge measuring device. For example, as illustrated in FIG. 25A, the system includes the measuring device 1000 as well as a distance guide 1024 along at least a portion of the length of the arm 1016. Thus, the system can be designed to provide size information for multiple different materials and objects that may be encountered during a procedure.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A medical tool comprising:
   a first arm comprising a first jaw at a first end of the first arm and a first finger grip at a second end of the first arm, the first jaw comprising a first gripping surface at a terminus of the first jaw and a first cutting edge adjacent to the first gripping surface;
   a second arm attached to the first arm at a pivot point the second arm comprising a second jaw at a first end of the second arm and a second finger grip at a second end of the second arm, the second jaw comprising a second gripping surface at a terminus of the second jaw and a second cutting edge adjacent to the second gripping surface, the first and second cutting edges being mated with one another as scissor blades, wherein relative motion between the first arm and the second arm at the pivot point defines an open position and a closed position, the first and second gripping surfaces meeting one another at the closed position;
   a gripping notch formed in the first arm or the second arm;
   a first distance guide extending along at least a portion of a length of the first arm or the second arm; and
   a measuring device attachable to the first arm between the first jaw and the first finger grip, the measuring device overlapping the pivot point and including a second distance guide that is correlated with the first and second arms such that an alignment between the first arm or the second arm and the second distance guide indicates a distance between the first and second gripping surfaces.

2. The medical tool of claim 1, the first distance guide including a first section extending along a portion of the length of the first arm and a second section extending along a portion of a length of the second arm.

3. The medical tool of claim 1, the first distance guide including distance markings in dimensions of centimeters, millimeters, inches, or combinations thereof.

4. The medical tool of claim 1, the first gripping surface differing from the second gripping surface.

5. The medical tool of claim 1, the first jaw further comprising a third gripping surface and the second jaw further comprising a fourth gripping surface.

6. The medical tool of claim 1, the measuring device that is attachable to the first arm, comprising an ornamental profile.

7. The medical tool of claim 1, the second distance guide including distance markings in dimensions of centimeters, millimeters, inches, or combinations thereof.

8. A medical tool comprising:
   a first arm comprising a first jaw at a first end of the first arm and a first finger grip at a second end of the first arm, the first jaw comprising a first gripping surface at a terminus of the first jaw and a first cutting edge adjacent to the first gripping surface;
   a second arm attached to the first arm at a pivot point, the second arm comprising a second jaw at a first end of the second arm and a second finger grip at a second end of the second arm, the second jaw comprising a second gripping surface at a terminus of the second jaw and a second cutting edge adjacent to the second gripping surface, the first and second cutting edges being mated with one another as scissor blades, wherein relative motion between the first arm and the second arm at the pivot point defines an open position and a closed position, the first and second gripping surfaces meeting one another at the closed position; and a measuring device attachable to the first arm between the first jaw and the first finger grip, the measuring device overlapping the pivot point and including a first distance guide that is correlated with the first and second arms such that an alignment between the first arm or the second arm and the first distance guide indicates a distance between the first and second gripping surfaces.

9. The medical tool of claim 8, the first gripping surface differing from the second gripping surface.

10. The medical tool of claim 8, the first jaw further comprising a third gripping surface and the second jaw further comprising a fourth gripping surface.

11. The medical tool of claim 8, further comprising a gripping notch formed in the first arm or the second arm.

12. The medical tool of claim 8, further comprising a second distance guide extending along at least a portion of a length of the first arm and/or the second arm.

13. The medical tool of claim 12, the second distance guide including a first section extending along a portion of the length of the first arm and a second section extending along a portion of a length of the second arm.

14. The medical tool of claim 12, the second distance guide including distance markings in dimensions of centimeters, millimeters, inches, or combinations thereof.

15. The medical tool of claim 8, the first distance guide including distance markings in dimensions of centimeters, millimeters, inches, or combinations thereof.

16. The medical tool of claim 8, the measuring device that is attachable to the first arm comprising an ornamental profile.

\* \* \* \* \*